United States Patent
Lyng et al.

(10) Patent No.: US 7,863,053 B2
(45) Date of Patent: Jan. 4, 2011

(54) SWAB-BASED DIAGNOSTIC SYSTEMS

(75) Inventors: Robert John Lyng, Norcross, GA (US); Jeffrey Eldon Fish, Dacula, GA (US); Rosann Marie Matthews Kaylor, Cumming, GA (US); Naveen Agarwal, Evansville, IN (US); Lei Huang, Duluth, GA (US); John Albert Shuty, Alpharetta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 605 days.

(21) Appl. No.: 10/744,607

(22) Filed: Dec. 23, 2003

(65) Prior Publication Data

US 2005/0136479 A1    Jun. 23, 2005

(51) Int. Cl.
*G01N 21/03*    (2006.01)

(52) U.S. Cl. .................. 436/165; 436/164; 435/7.1; 435/287.1; 435/287.2; 435/287.3; 435/288.5; 422/68.1

(58) Field of Classification Search .............. 422/50, 422/61, 68.1, 255, 256, 258, 261, 269–271, 422/292; 435/4, 7.1, 287.1, 287.2, 287.3, 435/288.2, 288.5, 810, 960, 970; 436/518, 436/164, 165

See application file for complete search history.

(56) References Cited

U.S. PATENT DOCUMENTS

| | | | |
|---|---|---|---|
| 3,792,699 A | 2/1974 | Tobin et al. | |
| 4,168,146 A | 9/1979 | Grubb et al. | |
| 4,235,601 A | 11/1980 | Deutsch et al. | |
| 4,366,241 A | 12/1982 | Tom et al. | |
| 4,386,128 A * | 5/1983 | Yoshikawa | 428/152 |
| 4,442,204 A | 4/1984 | Greenquist et al. | |
| 4,447,526 A * | 5/1984 | Rupchock et al. | 435/7.7 |
| 4,458,020 A * | 7/1984 | Bohn et al. | 435/287.2 |
| 4,707,450 A | 11/1987 | Nason | |
| 4,831,840 A * | 5/1989 | Fletcher | 62/356 |
| 4,952,204 A | 8/1990 | Korteweg | |
| 5,084,245 A | 1/1992 | Berke et al. | |
| 5,129,402 A | 7/1992 | Koll et al. | |
| 5,137,808 A | 8/1992 | Ullman et al. | |
| 5,208,535 A | 5/1993 | Nakayama et al. | |
| 5,238,649 A | 8/1993 | Nason | |

(Continued)

FOREIGN PATENT DOCUMENTS

EP    0354704 A1    2/1990

(Continued)

*Primary Examiner*—Melanie Yu
(74) *Attorney, Agent, or Firm*—Dority & Manning, P.A.

(57) ABSTRACT

A diagnostic test system for detecting the presence or absence of an analyte within a test sample is provided. For instance, the system may include a swab and a detection unit. The detection unit includes a first component that is capable of receiving the swab, the first component defining an insertion chamber within which a fluid is capable of being retained. The detection unit also includes a second component that defines a detection chamber within which an assay for detecting the presence or absence of the analyte is capable of being contained. The first component is rotatable relative to the second component from an inactive position to an active position. In the inactive position, the fluid remains substantially contained within the insertion chamber. In the active position, the fluid may flow from the insertion chamber to the detection chamber and contact the assay.

6 Claims, 6 Drawing Sheets

U.S. PATENT DOCUMENTS

| | | |
|---|---|---|
| 5,250,412 A | 10/1993 | Giegel |
| 5,266,266 A | 11/1993 | Nason |
| 5,278,075 A | 1/1994 | Stone |
| 5,295,952 A | 3/1994 | Pietrafitta |
| 5,330,917 A | 7/1994 | Stone |
| 5,364,792 A | 11/1994 | Stone |
| 5,395,754 A | 3/1995 | Lambotte et al. |
| 5,449,071 A | 9/1995 | Levy |
| 5,449,494 A | 9/1995 | Seeney |
| 5,508,171 A | 4/1996 | Walling et al. |
| 5,534,132 A | 7/1996 | Vreeke et al. |
| 5,550,061 A | 8/1996 | Stone |
| 5,660,990 A * | 8/1997 | Rao et al. .................. 435/6 |
| 5,670,381 A | 9/1997 | Jou et al. |
| 5,869,003 A * | 2/1999 | Nason .................. 422/58 |
| 5,879,635 A | 3/1999 | Nason |
| 5,917,592 A * | 6/1999 | Skiffington .................. 356/244 |
| 5,965,453 A | 10/1999 | Skiffington et al. |
| 5,983,438 A | 11/1999 | Bostick et al. |
| 6,043,047 A | 3/2000 | Foote et al. |
| 6,194,220 B1 | 2/2001 | Malick et al. |
| 6,197,254 B1 | 3/2001 | Silver et al. |
| 6,241,863 B1 | 6/2001 | Monbouquette |
| 6,248,294 B1 | 6/2001 | Nason |
| 6,270,637 B1 | 8/2001 | Crismore et al. |
| 6,281,006 B1 | 8/2001 | Heller et al. |
| 6,309,818 B1 | 10/2001 | Malinda et al. |
| 6,352,863 B1 | 3/2002 | Guirguis |
| 6,406,451 B1 | 6/2002 | Rowe |
| 6,436,651 B1 | 8/2002 | Everhart et al. |
| 6,461,496 B1 | 10/2002 | Feldman et al. |
| 6,524,530 B1 | 2/2003 | Igarashi et al. |
| 6,541,194 B2 * | 4/2003 | DiCesare .................. 435/4 |
| 6,548,018 B2 | 4/2003 | DiCesare |
| 6,565,808 B2 * | 5/2003 | Hudak et al. .................. 422/58 |
| 6,613,576 B1 | 9/2003 | Rodacy et al. |
| 2003/0119202 A1 | 6/2003 | Kaylor et al. |

FOREIGN PATENT DOCUMENTS

| | | |
|---|---|---|
| EP | 1234871 A1 | 8/2002 |
| WO | WO 9525948 A1 | 9/1995 |
| WO | WO 9614570 A1 | 5/1996 |
| WO | WO 9703209 A1 | 1/1997 |
| WO | WO 9723596 A1 | 7/1997 |
| WO | WO 9827196 A1 | 6/1998 |

* cited by examiner

US 7,863,053 B2

SWAB-BASED DIAGNOSTIC SYSTEMS

BACKGROUND OF THE INVENTION

Medical swabs are commonly used to collect biological specimens from a patient. Such medical swabs generally include a fibrous tip at one end of an elongated stick or shaft. Once a sample is collected, it may be transferred from the tip to a testing medium for performance of an immunoassay to determine the presence or absence of an analyte of interest. Some systems, known as "all-in-one" swab systems, have been developed that provide both the reagents for the immunoassay and the swab in a single, self-contained apparatus. However, one problem with such "all-in-one" systems is that the fluid contained within the apparatus often leaks out of the apparatus prior to use. In addition, the method for using such devices typically involves several complicated steps that may lower the real-time efficacy of the device in detecting the presence or absence of the analyte.

As such a need currently exits for a swab-based device that is effective in detecting the presence of an analyte in a simple manner.

SUMMARY OF THE INVENTION

In accordance with one embodiment of the present invention, a diagnostic test system is disclosed for detecting the presence or absence of an analyte within a test sample. The system comprises a swab and a detection unit. The detection unit comprises a first component that is capable of receiving the swab. In one embodiment, the first component defines a sample port through which the swab is capable of being inserted. A hydraulic seal (e.g., o-ring) may form a sealing fit between the sample port and the swab. The first component defines an insertion chamber within which a fluid is capable of being retained. In one embodiment, a flexible packet is contained within the insertion chamber, the flexible packet being configured to retain the fluid. For example, the flexible packet may be formed from a film, metallic foil, or combinations thereof. The flexible packet may have a thickness of less than about 0.05 inches, and in some embodiments, from about 0.0007 inches to about 0.02 inches.

The diagnostic test system also comprises a second component that defines a detection chamber within which an assay for detecting the presence or absence of the analyte is capable of being contained. The first component is rotatable relative to the second component from an inactive position to an active position. In the inactive position, the fluid remains substantially retained within the insertion chamber. In the active position, the fluid may flow from the insertion chamber to the detection chamber and contact the assay. In one embodiment, for instance, the system further comprises a delivery channel that is also rotatable relative to the second component. The second component may comprise a connection channel, wherein the delivery channel is capable of rotation into fluid communication with the connection channel so that the fluid flows from the insertion chamber, through the delivery channel, and into the connection channel. The connection channel may be in fluid communication with the detection chamber.

In accordance with another embodiment of the present invention, a method is disclosed for detecting the presence or absence of an analyte within a test sample. The method comprises:

i) providing a diagnostic test system, the system comprising a swab and a detection unit, the detection unit comprising:

a) a first component that is capable of receiving the swab, the first component defining an insertion chamber within which a fluid is retained; and b) a second component defining a detection chamber within which an assay for detecting the presence or absence of the analyte is capable of being contained;

ii) contacting the swab with the test sample;

iii) inserting the swab into the insertion chamber of the first component so that the swab contacts the fluid; and iv) rotating the first component relative to the second component so that the fluid flows from the insertion chamber to the detection chamber and contacts the assay. The method may further comprise determining the intensity of a detection signal generated at a detection zone of the assay, wherein the amount of the analyte within the test sample is determined from the detection signal. In addition, the detection signal may be calibrated by a calibration signal generated at a calibration zone of the assay, wherein the amount of the analyte within the test sample is determined from the detection signal as calibrated by the calibration signal.

Other features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

Figure 1:
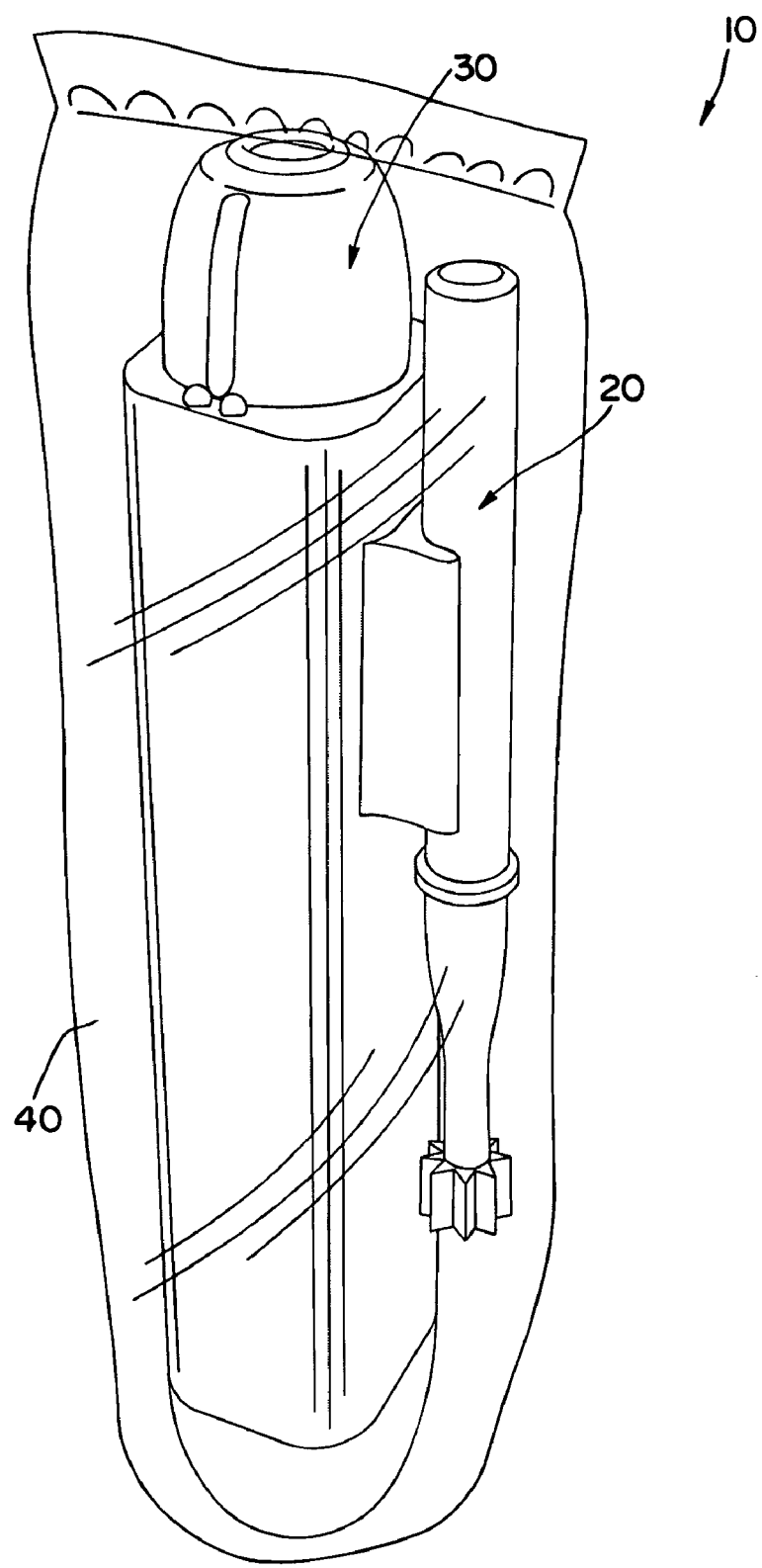
FIG. 1 is a perspective view of one embodiment of a diagnostic system of the present invention contained within a sealed package.

Repeat use of reference characters in the present specification and drawings is intended to represent same or analogous features or elements of the invention.

DETAILED DESCRIPTION OF REPRESENTATIVE EMBODIMENTS

Definitions

As used herein, the term "analyte" generally refers to a substance to be detected. For instance, analytes may include antigenic substances, haptens, antibodies, and combinations thereof. Analytes include, but are not limited to, toxins, organic compounds, proteins, peptides, microorganisms, amino acids, nucleic acids, hormones, steroids, vitamins, drugs (including those administered for therapeutic purposes as well as those administered for illicit purposes), drug intermediaries or byproducts, bacteria, virus particles and metabolites of or antibodies to any of the above substances. Specific examples of some analytes include ferritin; creatinine kinase MB (CK-MB); digoxin; phenytoin; phenobarbitol; carbamazepine; vancomycin; gentamycin; theophylline; valproic acid; quinidine; luteinizing hormone (LH); follicle stimulating hormone (FSH); estradiol, progesterone; C-reactive protein; lipocalins; IgE antibodies; cytokines; vitamin B2 microglobulin; glycated hemoglobin (Gly. Hb); cortisol; digitoxin; N-acetylprocainamide (NAPA); procainamide; antibodies to rubella, such as rubella-IgG and rubella IgM; antibodies to toxoplasmosis, such as toxoplasmosis IgG (Toxo-IgG) and toxoplasmosis IgM (Toxo-IgM); testosterone; salicylates; acetaminophen; hepatitis B virus surface antigen (HBsAg); antibodies to hepatitis B core antigen, such as anti-hepatitis B core antigen IgG and IgM (Anti-HBC); human immune deficiency virus 1 and 2 (HIV 1 and 2); human T-cell leukemia virus 1 and 2 (HTLV); hepatitis B e antigen (HBeAg); antibodies to hepatitis B e antigen (Anti-HBe); influenza virus; thyroid stimulating hormone (TSH); thyroxine (T4); total triiodothyronine (Total T3); free triiodothyronine (Free T3); carcinoembryoic antigen (CEA); lipoproteins, cholesterol, and triglycerides; and alpha fetoprotein (AFP). Drugs of abuse and controlled substances include, but are not intended to be limited to, amphetamine; methamphetamine; barbiturates, such as amobarbital, secobarbital, pentobarbital, phenobarbital, and barbital; benzodiazepines, such as librium and valium; cannabinoids, such as hashish and marijuana; cocaine; fentanyl; LSD; methaqualone; opiates, such as heroin, morphine, codeine, hydromorphone, hydrocodone, methadone, oxycodone, oxymorphone and opium; phencyclidine; and propoxyhene. Other potential analytes may be described in U.S. Pat. No. 6,436,651 to Everhart. et al. and U.S. Pat. No. 4,366,241 to Tom et al.

As used herein, the term "test sample" generally refers to a material suspected of containing the analyte. The test sample may be used directly as obtained from the source or following a pretreatment to modify the character of the sample. The test sample may be derived from any biological source, such as a physiological fluid, including, blood, interstitial fluid, saliva, ocular lens fluid, cerebral spinal fluid, sweat, urine, milk, ascites fluid, mucous, synovial fluid, peritoneal fluid, vaginal fluid, amniotic fluid or the like. The test sample may be pretreated prior to use, such as preparing plasma from blood, diluting viscous fluids, and the like. Methods of treatment may involve filtration, precipitation, dilution, distillation, mixing, concentration, inactivation of interfering components, and the addition of reagents. Besides physiological fluids, other liquid samples may be used such as water, food products and the like for the performance of environmental or food production assays. In addition, a solid material suspected of containing the analyte may be used as the test sample. In some instances it may be beneficial to modify a solid test sample to form a liquid medium or to release the analyte.

Detailed Description

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention covers such modifications and variations as come within the scope of the appended claims and their equivalents.

Figure 2:
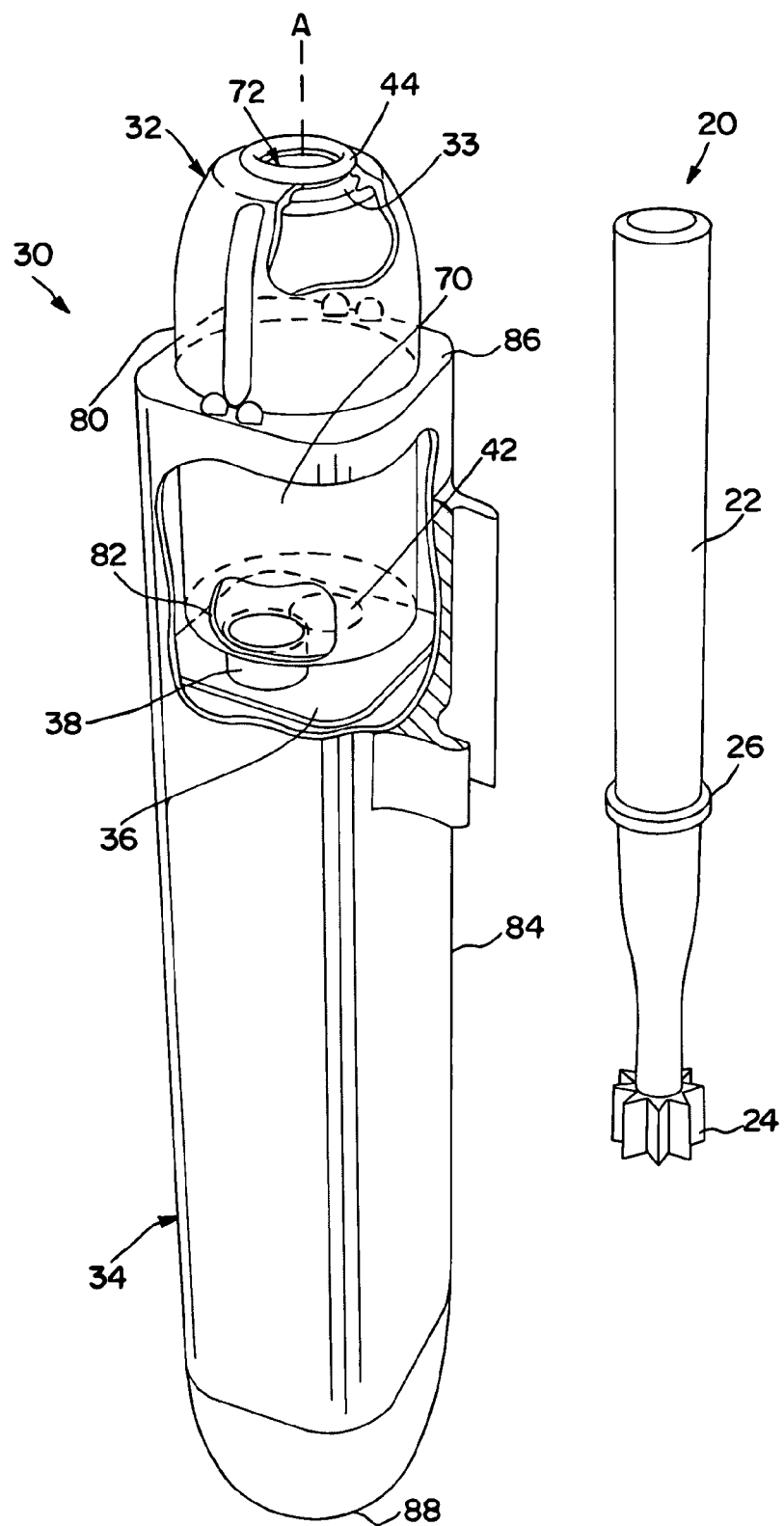
FIG. 2 is a perspective view of one embodiment of a diagnostic system of the present invention with the swab and test unit shown separately.

Referring to FIGS. 1-2, for instance, one embodiment of a diagnostic test system 10 that may be formed according to the present invention will now be described in more detail. As shown, the system 10 includes a swab 20 and a detection unit 30 into which the swab 20 may be inserted. The swab 20 and/or detection unit 30 may optionally be sealed within a package 40. The configuration of the swab 20 (e.g., shape, size, materials, etc.) may generally vary as is well known in the art. For example, in the illustrated embodiment, the swab 20 includes an elongated shaft 22 having a tip 24 of an absorbent material, such as cotton or rayon, at one end. It should be understood that the tip 24 may also be formed from any other absorbent material known in the art, and may possess any desired shape and/or size. Further, any other swab construction, as well as any other type of test sample collection device, may also be used in the present invention. For example, other types of test sample collection devices are described in U.S. Pat. No. 6,541,194 to DiCesare and U.S. Pat. No. 6,548,018 to DiCesare, et al., which are incorporated herein in their entirety by reference thereto for all purposes.

The detection unit 30 is generally of a size and shape to enable easy manual handling during use. In the illustrated embodiment, for example, the detection unit 30 is substantially cylindrical in shape and is formed from at least two components that extend along a longitudinal axis A, i.e., a first component 32 in fluid communication with a second component 34. The first and second components 32 and 34 may be made from any of a variety of materials, such as molded or blown plastic. In addition, the first and second components 32 and 34 may also have a variety of different shapes and/or sizes. In the illustrated embodiment, for instance, the first component 32 has a generally cylindrical shape defined by an enclosure 80 that begins at a generally circular lower portion 82 and ends at the sample port 72, wherein the width (e.g., diameter) of the component 32 is greater at the lower portion 82 than at the port 72. Similarly, the second component 34 also has a generally cylindrical shape defined by an enclosure 84 that begins at a generally rectangular upper portion 86 and ends at the bottom end 88 of the detection unit 30, wherein the width of the component 34 is greater at the upper portion 86 than at the bottom end 88. The detection unit 30 has a length that allows the swab absorbent tip 24 to be fully immersed in the reagents involved, which may be determined by the amount of reagent that is required. Example volumes of the reagents are from about 50 to about 1000 microliters of fluid, with a typical amount being from about 100 to about 200 microliters.

The first component 32 defines a hollow insertion chamber 70 into which the swab 20 may be easily inserted via a sample port 72. The insertion chamber 70 may be provided with a fluid for mixing with a test sample contained on the swab 20. For example, the fluid may be a buffer fluid, such as phosphate-buffered saline (PBS) (e.g., pH of 7.2) or 2-(N-morpholino) ethane sulfonic acid (MES) (e.g., pH of 5.3). Other types of fluids that may be contained within the device include detergents, salts, lysing agents (such as for detection of microbes, e.g., Strep bacteria or yeasts), blocking agents (e.g., bovine serum albumin), other proteins, and so forth. Still other optional materials that may be present within the fluid include labeled microparticles, detection probes, dyes, electrochemically-active agents (e.g., redox mediators), or other reagents used to create a signal for detection.

To inhibit leaking of the fluid from the sample port 72, various mechanisms may be employed. For example, prior to insertion of the swab 20, a top or cap may cover the sample port 72. In addition, the fluid within the insertion chamber 70 may also be retained within a thin, flexible packet (not shown) that is relatively resistant to diffusion of the fluid therethrough. The packet may be formed from a variety of different materials, such as nonporous films, metallic seals (e.g., aluminum foil), etc. Some suitable materials used in the fabrication of films for forming the packet may include thermoplastic polymers, such as polyolefins (e.g., polyethylene, polypropylene, etc.), including homopolymers, copolymers, terpolymers and blends thereof; ethylene vinyl acetate; ethylene ethyl acrylate; ethylene acrylic acid; ethylene methyl acrylate; ethylene normal butyl acrylate; polyurethane; poly(ether-ester); poly(amid-ether) block copolymers; and the like. Other suitable materials may include non-thermoplastic materials, silicone-based materials, other elastomeric materials, and so forth. In some embodiments, it is desired to minimize the thickness of the packet so that a user may easily rupture it with the swab 20. In such instances, the thickness of the packet may be less than about 0.05 inches, in some embodiments between about 0.0003 inches to about 0.01 inches, and in some embodiments, between about 0.0007 inches to about 0.02 inches.

In addition, mechanisms may also be employed to inhibit fluid leakage from the sample port 72 after insertion of the swab 20 into the insertion chamber 70. For example, as shown in FIG. 2, the first component 32 may utilize a hydraulic seal, such as o-rings 33 and 44. As is well known in the art, the o-rings 33 and 44 provide a sealing fit between the outer surface of the swab 20 and the inner surface of the sample port 72. Other known hydraulic seals, such as t-rings, d-rings, v-rings, etc., may also be used in the present invention. Using such seals, unwanted leakage from the sample port 72 may be inhibited.

As indicated above, the first component 32 is in fluid communication with a second component 34. In this embodiment, for example, the first component 32 generally rotates about the longitudinal axis A relative to the second component 34. Rotation may be accomplished manually, or through any well known automated device known in the art, including well known electronics, timing circuitry, etc. Due to the relative rotation of the components 32 and 34, a user may easily manipulate the components as desired so that they are placed in direct engagement. Namely, the detection unit 30 contains a delivery channel 38 that is also capable of rotation about the longitudinal axis A, which is formed integral with or separate from the first component 32. In the illustrated embodiment, for example, the delivery channel 38 is connected to the lower portion 82 of the first component 32.

When not in use, the first component 32 and delivery channel 38 are positioned so that fluid within the insertion chamber 70 does not flow to a detection chamber 73 of the second component 34, i.e., inactive position. In one embodiment, for instance, this prohibitive function is accomplished by a barrier 36, which may have any suitable size and/or shape, and be formed from any suitable material known in the art. For example, in one embodiment, the barrier 36 is formed from a liquid-impermeable polymeric material. To engage the first component 32 with the second component 34, the first component 32 is rotated so that the delivery channel 38 is positioned adjacent to a connection channel 42 of the second component 34, i.e., active position. Consequently, fluid is capable of flowing from the chamber 70, through the delivery channel 38 and connection channel 42, and finally into the detection chamber 73.

Figure 3:
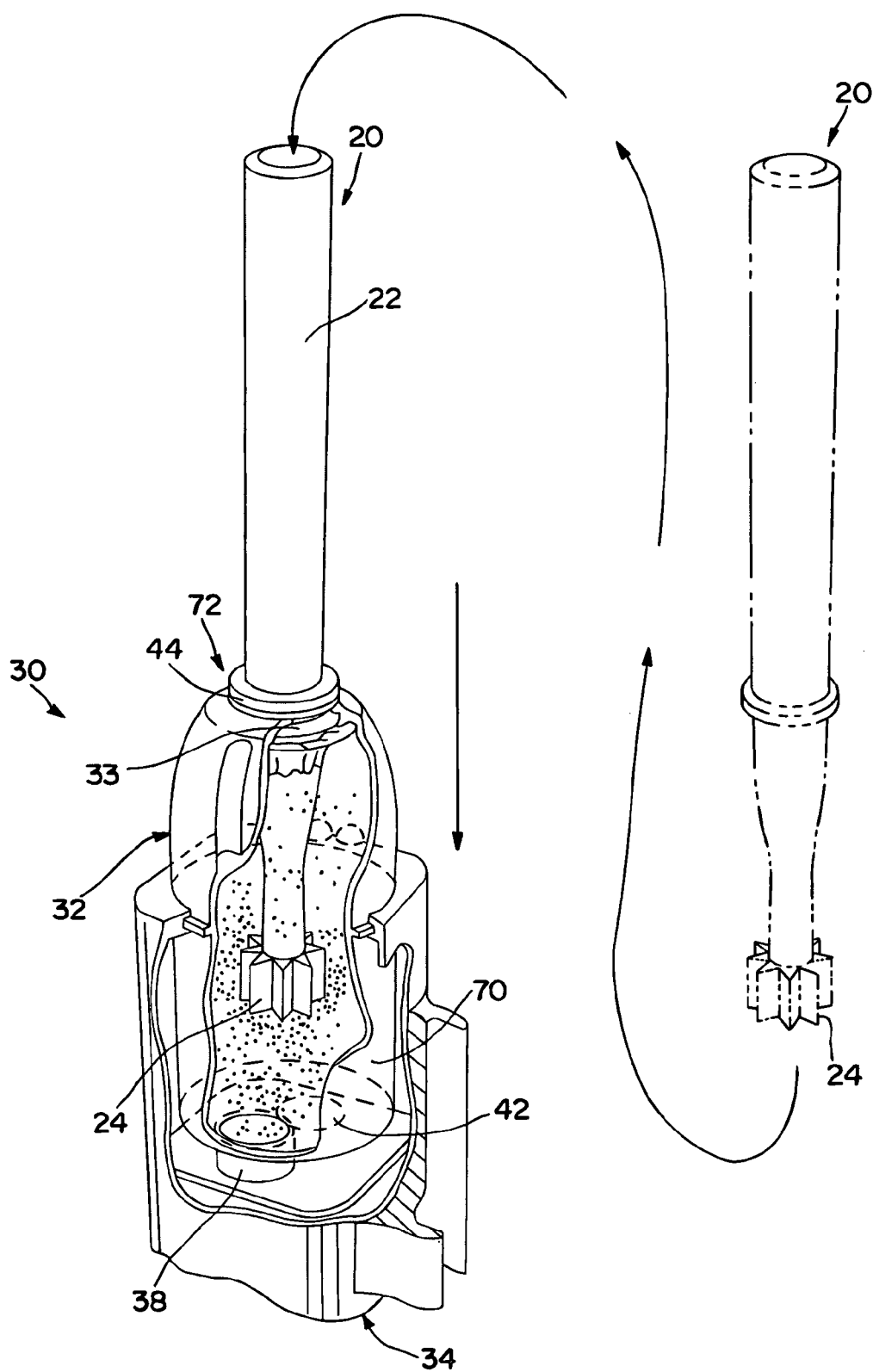
FIG. 3 is a perspective view depicting insertion of a swab into the test unit shown in FIG. 2.
Figure 4:
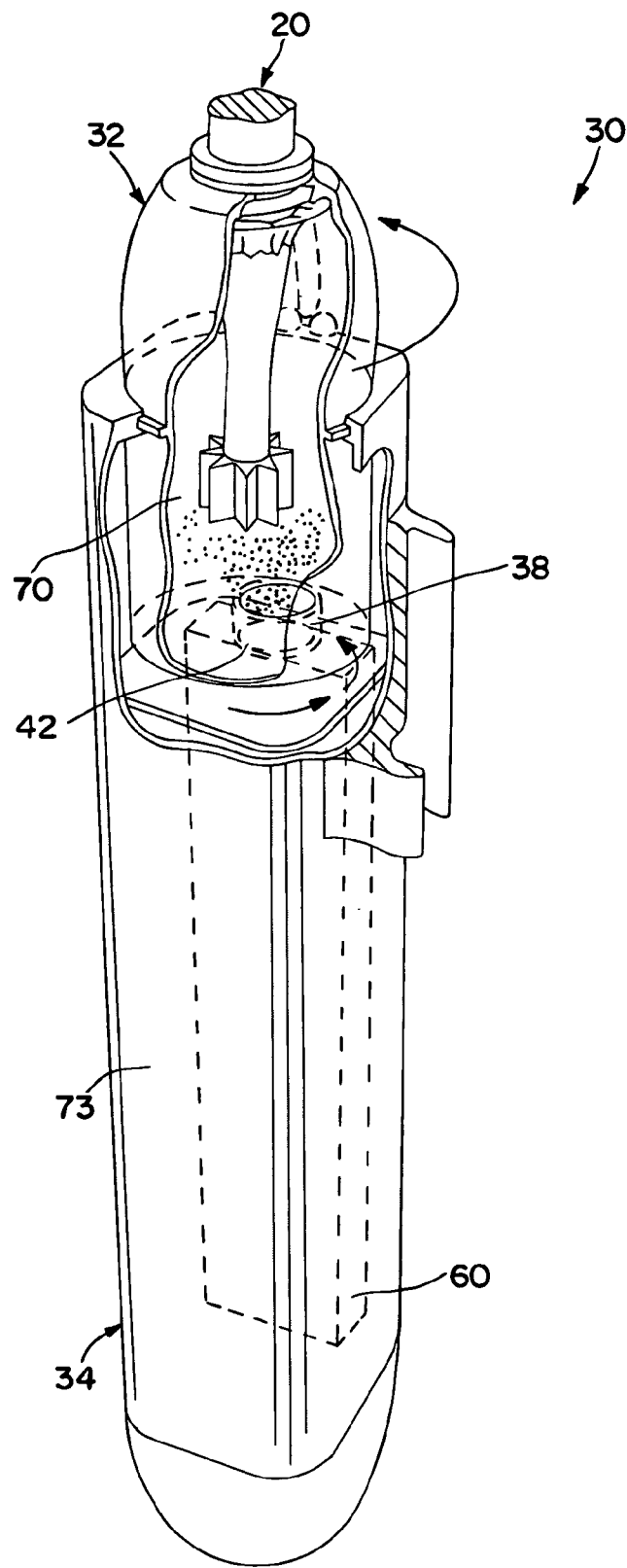
FIG. 4 is a perspective view depicting rotation of the test unit shown in FIG. 2.
Figure 5:
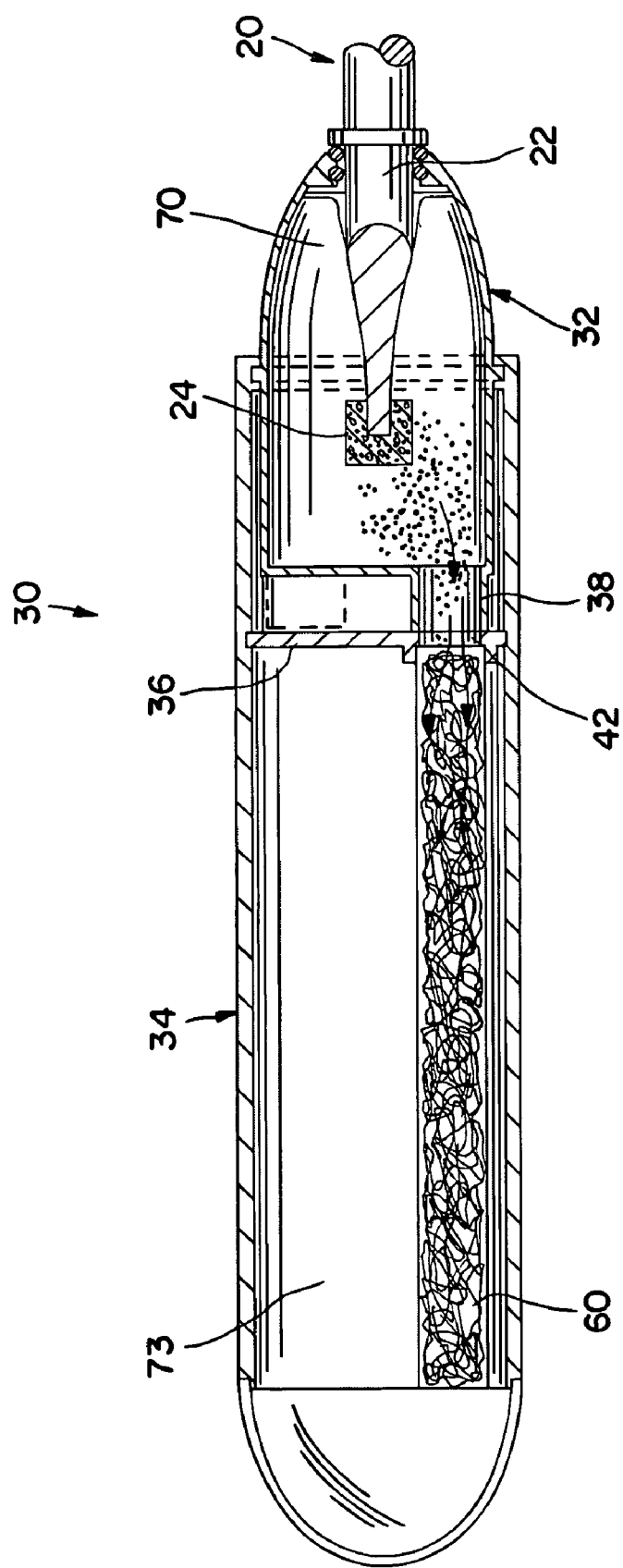
FIG. 5 is a cross-sectional view of the rotated test unit depicted in FIG. 4.

Referring to FIGS. 3-5, the operation of the diagnostic test system 10 will now be described in more detail. Initially, the tip 24 of the swab 20 is contacted with a test sample suspected of containing the analyte of interest. Thereafter, as represented by the directional arrows of FIG. 3, the tip 24 is inserted through the sample port 72. Upon insertion, the o-rings 33 and 44 form a fitting seal around the elongated shaft 22 of the swab 20. As described above, insertion of the tip 24 may also cause a thin, flexible packet (not shown) within the insertion chamber 70 to rupture, thereby releasing a fluid retained therein to mix with the test sample. Once the swab 20 is inserted and optionally allowed to mix with a fluid within the insertion chamber 70, the first component 32 may then be placed into engagement with the second component 34. The engagement of the two components is illustrated in FIG. 4. Specifically, in this embodiment, the first component 32 is rotated in a counter-clockwise direction so that the delivery channel 38 is placed into communication with the connection channel 42. In this manner, fluid may flow from the insertion chamber 70 into a detection chamber 73 of the second component 34. Once in the detection chamber 73, the fluid is allowed to contact an assay 60 for detecting the presence or absence of the analyte of interest.

Figure 6:
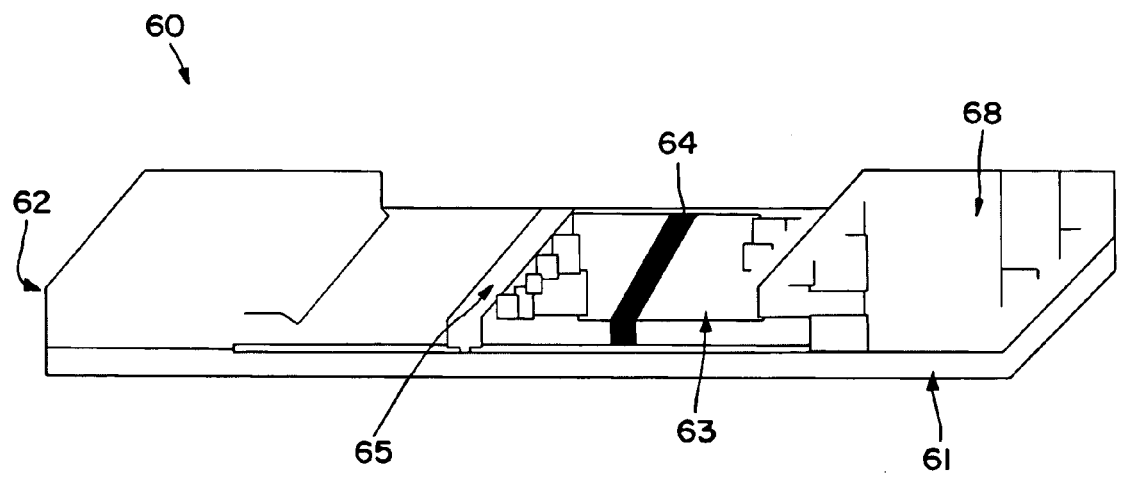
FIG. 6 is a perspective view of an assay that may be utilized in one embodiment of the present invention.

For purposes of illustration only, various examples of an assay (or "assay device") 60 that may be used in conjunction with the diagnostic test system 10 will now be described in more detail. It should be understood, however, that other assays are also contemplated by the present invention. In fact, the present invention is not limited to any particular assay configuration. In this regard, referring to FIG. 6, one embodiment of an assay 60 is illustrated that is an immunoassay. Immunoassays utilize mechanisms of the immune systems, wherein antibodies are produced in response to the presence of antigens that are pathogenic or foreign to the organisms. These antibodies and antigens, i.e., immunoreactants, are capable of binding with one another, thereby causing a highly specific reaction mechanism that may be used to determine the presence or concentration of that particular antigen in a biological sample.

In the illustrated embodiment, the assay 60 contains a porous membrane 63 optionally supported by a rigid material 61. In general, the porous membrane 63 may be made from any of a variety of materials through which a fluid is capable of passing. For example, the materials used to form the porous membrane 63 may include, but are not limited to, natural, synthetic, or naturally occurring materials that are synthetically modified, such as polysaccharides (e.g., cellulose materials such as paper and cellulose derivatives, such as cellulose acetate and nitrocellulose); polyether sulfone; polyethylene; nylon; polyvinylidene fluoride (PVDF); polyester; polypropylene; silica; inorganic materials, such as deactivated alumina, diatomaceous earth, $MgSO_4$, or other inorganic finely divided material uniformly dispersed in a porous polymer matrix, with polymers such as vinyl chloride, vinyl chloride-propylene copolymer, and vinyl chloride-vinyl acetate copolymer; cloth, both naturally occurring (e.g., cotton) and synthetic (e.g., nylon or rayon); porous gels, such as silica gel, agarose, dextran, and gelatin; polymeric films, such as polyacrylamide; and the like. In one particular embodiment, the porous membrane 63 is formed from nitrocellulose and/or polyether sulfone materials. It should be understood that the term "nitrocellulose" refers to nitric acid esters of cellulose, which may be nitrocellulose alone, or a mixed ester of nitric acid and other acids, such as aliphatic carboxylic acids having from 1 to 7 carbon atoms.

The assay 60 may also contain an absorbent pad 68. The absorbent pad 68 generally receives fluid that has migrated through the entire porous membrane 63. As is well known in the art, the absorbent pad 68 may assist in promoting capillary action and fluid flow through the membrane 63. In some embodiments, the fluid from the connection channel 42 (see FIGS. 1-5) may first contact a sample pad (not shown) that is in fluid communication with the porous membrane 63. Some suitable materials that may be used to form the sample pad include, but are not limited to, nitrocellulose, cellulose, porous polyethylene pads, and glass fiber filter paper. If desired, the sample pad may also contain one or more assay pretreatment reagents, either diffusively or non-diffusively attached thereto.

In the illustrated embodiment, the test sample travels from the sample pad (not shown) to a conjugate pad 62 that is placed in communication with one end of the sampling pad. The conjugate pad 62 is formed from a material through which a fluid is capable of passing. For example, in one embodiment, the conjugate pad 62 is formed from glass fibers. Although only one conjugate pad 62 is shown, it should be understood that other conjugate pads may also be used in the present invention.

To facilitate detection of the presence or absence of an analyte within the test sample, various detection probes may be applied to the conjugate pad 62. While contained on the conjugate pad 62, these detection probes remain available for binding with the analyte as it passes from the sampling pad through the conjugate pad 62 (or optionally in diluent). Upon binding with the analyte, the detection probes may later serve to identify the presence or absence of the analyte. The detection probes may be used for both detection and calibration of the assay 60. In alternative embodiments, however, separate calibration probes may be applied to the conjugate pad 62 for use in conjunction with the detection probes to facilitate simultaneous calibration and detection, thereby eliminating inaccuracies often created by conventional assay calibration systems. It should be understood, however, that the detection probes and/or the calibration probes may be applied together or separately at any location of the assay 60, and need not be applied to the conjugate pad 62. Further, it should also be understood that the detection probes and/or the calibration probes may be applied to the same or different conjugate pads.

In some instances, it is desired to modify the detection probes in some manner so that they are more readily able to bind to the analyte. In such instances, the detection probes may be modified with certain specific binding members that are adhered thereto to form conjugated probes. Specific binding members generally refer to a member of a specific binding pair, i.e., two different molecules where one of the molecules chemically and/or physically binds to the second molecule. For instance, immunoreactive specific binding members may include antigens, haptens, aptamers, antibodies (primary or secondary), and complexes thereof, including those formed by recombinant DNA methods or peptide synthesis. An antibody may be a monoclonal or polyclonal antibody, a recombinant protein or a mixture(s) or fragment(s) thereof, as well as a mixture of an antibody and other specific binding members. The details of the preparation of such antibodies and their suitability for use as specific binding members are well known to those skilled in the art. Other common specific binding pairs include but are not limited to, biotin and avidin (or derivatives thereof), biotin and streptavidin, carbohydrates and lectins, complementary nucleotide sequences (including probe and capture nucleic acid sequences used in DNA hybridization assays to detect a target nucleic acid sequence), complementary peptide sequences including those formed by recombinant methods, effector and receptor molecules, hormone and hormone binding protein, enzyme cofactors and enzymes, enzyme inhibitors and enzymes, and so forth. Furthermore, specific binding pairs may include members that are analogs of the original specific binding member. For example, a derivative or fragment of the analyte, i.e., an analyte-analog, may be used so long as it has at least one epitope in common with the analyte.

The specific binding members may generally be attached to the detection probes using any of a variety of well-known techniques. For instance, covalent attachment of the specific binding members to the detection probes (e.g., particles) may be accomplished using carboxylic, amino, aldehyde, bromoacetyl, iodoacetyl, thiol, epoxy and other reactive or linking functional groups, as well as residual free radicals and radical cations, through which a protein coupling reaction may be accomplished. A surface functional group may also be incorporated as a functionalized co-monomer because the surface of the detection probe may contain a relatively high surface concentration of polar groups. In addition, although detection probes are often functionalized after synthesis, in certain cases, such as poly(thiophenol), the probes are capable of direct covalent linking with a protein without the need for further modification. Besides covalent bonding, other attachment techniques, such as physical adsorption, may also be utilized.

In one embodiment, for instance, the fluid containing the test sample travels to the conjugate pad 62, where the analyte mixes with detection probes modified with a specific binding member to form analyte complexes. Because the conjugate pad 62 is in fluid communication with the porous membrane 63, the complexes may migrate from the conjugate pad 62 to a detection zone 65 present on the porous membrane 63. The detection zone 65 may contain an immobilized receptive material that is generally capable of forming a chemical or physical bond with the analyte and/or complexes thereof (e.g., complexes of the analyte with the detection probes). In some embodiments, the receptive material may be a biological receptive material. Such biological receptive materials are well known in the art and may include, but are not limited to, antigens, haptens, antibodies, protein A or G, avidin, streptavidin, and complexes thereof. In some cases, it is desired that these biological receptive materials are capable of binding to the analyte and/or the complexes of the analyte with the detection probes.

These receptive materials serve as stationary binding sites for the detection probe/analyte complexes. In some instances, the analytes, such as antibodies, antigens, etc., have two binding sites. Upon reaching the detection zone 65, one of these binding sites is occupied by the specific binding member of the complexed probes. However, the free binding site of the analyte may bind to the immobilized receptive material. Upon being bound to the immobilized receptive material, the complexed probes form a new ternary sandwich complex.

The detection zone 65 may generally provide any number of distinct detection regions so that a user may better determine the concentration of a particular analyte within a test sample. Each region may contain the same receptive materials, or may contain different receptive materials for capturing multiple analytes. For example, the detection zone 65 may include two or more distinct detection regions (e.g., lines, dots, etc.). The detection regions may be disposed in the form of lines in a direction that is substantially perpendicular to the flow of the test sample through the assay 60. Likewise, in some embodiments, the detection regions may be disposed in the form of lines in a direction that is substantially parallel to the flow of the test sample through the assay device.

Although the detection zone 65 may indicate the presence of an analyte, it is often difficult to determine the relative concentration of the analyte within the test sample using solely a detection zone 65. Thus, the assay 60 may also include a calibration zone 64. In this embodiment, the calibration zone 64 is formed on the porous membrane 63 and is positioned downstream from the detection zone 65. The calibration zone 64 is provided with a receptive material that is capable of binding to any remaining uncaptured detection probes and/or calibration probes that pass through the length of the membrane 63. In particular, upon being contacted with the test sample, any uncaptured probes that do not bind to the analyte migrate through the detection zone 65 and enter the calibration zone 64 of the porous membrane 63. At the calibration zone 64, these uncaptured probes then bind to the receptive materials.

The receptive materials utilized in the calibration zone 64 may be the same or different than the receptive materials used in the detection zone 65. For instance, in some embodiments, the receptive material may include a polyelectrolyte that may bind to the uncaptured probes. The polyelectrolytes may have a net positive or negative charge, as well as a net charge that is generally neutral. For instance, some suitable examples of polyelectrolytes having a net positive charge include, but are not limited to, polylysine (commercially available from Sigma-Aldrich Chemical Co., Inc. of St. Louis, Mo.), polyethylenimine; epichlorohydrin-functionalized polyamines and/or polyamidoamines, such as poly(dimethylamine-co-epichlorohydrin); polydiallyldimethyl-ammonium chloride; cationic cellulose derivatives, such as cellulose copolymers or cellulose derivatives grafted with a quaternary ammonium water-soluble monomer; and the like. In one particular embodiment, CelQuat® SC-230M or H-100 (available from National Starch & Chemical, Inc.), which are cellulosic derivatives containing a quaternary ammonium water-soluble monomer, may be utilized. Moreover, some suitable examples of polyelectrolytes having a net negative charge include, but are not limited to, polyacrylic acids, such as poly(ethylene-co-methacrylic acid, sodium salt), and the like. It should also be understood that other polyelectrolytes may also be utilized in the present invention, such as amphiphilic polyelectrolytes (i.e., having polar and non-polar portions). For instance, some examples of suitable amphiphilic polyelectrolytes include, but are not limited to, poly(styryl-b-N-methyl 2-vinyl pyridinium iodide) and poly(styryl-b-acrylic acid), both of which are available from Polymer Source, Inc. of Dorval, Canada.

Similar to the detection zone 65, the calibration zone 64 may also provide any number of distinct calibration regions in any direction so that a user may better determine the concentration of a particular analyte within a test sample. The calibration regions may be pre-loaded on the porous membrane 63 with different amounts of the binder so that a different signal intensity is generated by each calibration region upon migration of the uncaptured probes. The overall amount of receptive material within each calibration region may be varied by utilizing calibration regions of different sizes and/or by varying the concentration or volume of the binder in each calibration region. If desired, an excess of probe molecules may be employed in the assay 60 so that each calibration region reaches its full and predetermined potential for signal intensity. That is, the amount of uncaptured probes that are deposited upon calibration regions are predetermined because the amount of the binder employed on the calibration regions is set at a predetermined and known level. Once captured, the signal of the probes at the detection and calibration zones 65 and 64 may be measured visually or through other methods of detection (e.g., instruments). When determined visually, for instance, a portion of the enclosure 84 of the second component 34 may optionally be provided with a window or other viewing area (not shown) as is well known in the art so that a user may readily observe the assay 60.

In some cases, the membrane 63 may also define a control zone (not shown) that gives a signal to the user that the assay is performing properly. For instance, the control zone (not shown) may contain an immobilized receptive material that is generally capable of forming a chemical and/or physical bond with probes or with the receptive material immobilized on the probes. Some examples of such receptive materials include, but are not limited to, antigens, haptens, antibodies, protein A or G, avidin, streptavidin, secondary antibodies, and complexes thereof. In addition, it may also be desired to utilize various non-biological materials for the control zone receptive material. For instance, in some embodiments, the control zone receptive material may also include a polyelectrolyte, such as described above, that may bind to uncaptured probes. Because the receptive material at the control zone is only specific for probes, a signal forms regardless of whether the analyte is present. The control zone may be positioned at any location along the membrane 63, but is preferably positioned upstream from the detection zone 65.

Various formats may be used to test for the presence or absence of an analyte using the assay 60. For instance, in the embodiment described above, a "sandwich" format is utilized. Other examples of such sandwich-type assays are described by U.S. Pat. No. 4,168,146 to Grubb, et al. and U.S. Pat. No. 4,366,241 to Tom, et al., which are incorporated herein in their entirety by reference thereto for all purposes. In addition, other formats, such as "competitive" formats, may also be utilized. In a competitive assay, the labeled probe is generally conjugated with a molecule that is identical to, or an analogue of, the analyte. Thus, the labeled probe competes with the analyte of interest for the available receptive material. Competitive assays are typically used for detection of analytes such as haptens, each hapten being monovalent and capable of binding only one antibody molecule. Examples of competitive immunoassay devices are described in U.S. Pat. No. 4,235,601 to Deutsch, et al., U.S. Pat. No. 4,442,204 to Liotta, and U.S. Pat. No. 5,208,535 to Buechler, et al., which are incorporated herein in their entirety by reference thereto for all purposes. Various other device configurations and/or assay formats are also described in U.S. Pat. No. 5,395,754 to Lambotte, et al.; U.S. Pat. No. 5,670,381 to Jou, et al.; and U.S. Pat. No. 6,194,220 to Malick, et al., which are incorporated herein in their entirety by reference thereto for all purposes.

In addition, it should be understood that any known detection technique may be utilized in the present invention. For example, as is well known in the art, the assay 60 may also be an electrochemical affinity assay, which detects an electrochemical reaction between an analyte (or complex thereof) and a capture ligand on an electrode strip. For example, various electrochemical assays are described in U.S. Pat. No. 5,508,171 to Walling, et al.; U.S. Pat. No. 5,534,132 to Vreeke, et al.; U.S. Pat. No. 6,241,863 to Monbouguette; U.S. Pat. No. 6,270,637 to Crismore, et al.; U.S. Pat. No. 6,281,006 to Heller, et al.; and U.S. Pat. No. 6,461,496 to Feldman, et al., which are incorporated herein in their entirety by reference thereto for all purposes.

It has been discovered that the system of the present invention provides a relatively simple, compact and cost-efficient device for facilitated collecting and substantially immediate on-site testing of analytes. The system enables quick and easy specimen collection with a swab, followed by prompt placement of the collected specimen into a test unit that is substantially closed and sealed to minimize risk of direct personnel contact with the collected organism. Thereafter, the test unit may be manipulated to analyze the collected specimen and provide a visible test result. This visible test result may be readily observed by the person performing the test in a prompt manner and under test conditions conducive to highly reliable and consistent test results. After initial specimen collection, human contact with the specimen is thus substantially precluded throughout the test protocol, and the entire device with the collected specimen safely contained therein may be discarded as a unit when the test is concluded.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A diagnostic test system for detecting the presence or absence of an analyte within a test sample, the system comprising a swab for collecting the test sample and a detection unit, the detection unit comprising:
    a first component that includes an insertion chamber within which a fluid is capable of being retained, the swab being insertable into the insertion chamber through a sample port;
    a hydraulic seal that is capable of forming a sealing fit between the sample port and the swab;
    a flexible packet that is capable of retaining the fluid within the insertion chamber;
    a second component that includes a connection channel in fluid communication with a detection chamber, wherein an assay device is positioned within the detection chamber, wherein the first component, second component, and assay device extend along a longitudinal axis; and
    wherein rotation of the first component about the longitudinal axis relative to the second component allows the fluid to flow from the insertion chamber, through the connection channel, and into the detection chamber to contact the assay device.

2. The diagnostic test system of claim 1, further comprising a delivery channel in fluid communication with the insertion chamber, wherein rotation of the first component relative to the second component places the delivery channel into fluid communication with the connection channel to allow the fluid to flow from the insertion chamber to the detection chamber.

3. The diagnostic test system of claim 2, wherein the delivery channel is connected to the first component.

4. The diagnostic test system of claim 1, further comprising a barrier that is positioned between the connection channel and the detection chamber prior to rotation of the first component relative to the second component, the barrier inhibiting the flow of the fluid from the insertion chamber to the detection chamber.

5. The diagnostic test system of claim 1, wherein the flexible packet is formed from a film, metallic foil, or combinations thereof.

6. The diagnostic test system of claim 1, wherein the first component and the second component have a generally cylindrical shape.

\* \* \* \* \*